United States Patent
Obara et al.

(10) Patent No.: US 6,553,323 B1
(45) Date of Patent: Apr. 22, 2003

(54) METHOD AND ITS APPARATUS FOR INSPECTING A SPECIMEN

(75) Inventors: Kenji Obara, Yokohama (JP); Yuji Takagi, Kamakura (JP); Toshifumi Honda, Yokohama (JP); Ryo Nakagaki, Kawasaki (JP); Toshiei Kurosaki, Hitachinaka (JP); Yasuhiko Ozawa, Abiko (JP)

(73) Assignee: Hitachi, Ltd., Tokyo (JP)

( * ) Notice: Subject to any disclaimer, the term of this patent is extended or adjusted under 35 U.S.C. 154(b) by 89 days.

(21) Appl. No.: 09/661,182

(22) Filed: Sep. 13, 2000

(30) Foreign Application Priority Data

Sep. 17, 1999 (JP) .......................... 11-264164

(51) Int. Cl.⁷ ............................... G01B 5/28
(52) U.S. Cl. .................. 702/35; 382/141; 356/237.1
(58) Field of Search ................ 702/35; 382/141, 382/144, 147, 150, 149; 356/237.1, 237.5, 237.3, 239.8, 237.2, 237.4

(56) References Cited

U.S. PATENT DOCUMENTS 4,428,235 A * 1/1984 Sugiyama ..................... 73/574
5,355,212 A * 10/1994 Wells et al. ............. 356/237.4
5,446,584 A * 8/1995 Bacchi et al. ............... 359/391
5,598,341 A * 1/1997 Ling et al. ................... 700/110
6,047,083 A * 4/2000 Mizuno ......................... 348/87

FOREIGN PATENT DOCUMENTS

JP 10135288 5/1998

* cited by examiner

*Primary Examiner*—Bryan Bui
*Assistant Examiner*—Hien Vo
(74) *Attorney, Agent, or Firm*—Townsend and Townsend and Crew LLP

(57) ABSTRACT

The present invention improves inspection efficiency in detailed inspections of defects performed based on inspection information from a defect inspection. Particles and defects are detected by a defect inspection device 1. If the cause of the particles and defects are to be determined by performing a detailed inspection with a details inspection device 3 using an SEM or the like, attributes are determined on the particles and defects detected by the defects inspection device 1 before the detailed inspection is performed. The attributes are determined with an attribute inspection device using an optical microscope or the like. Based on these attributes, the defects and particles are separated into those that require detailed inspection and those that do not require detailed inspection or that cannot be inspected in detail. A details inspection device 3 is used to inspect the particles and defects requiring detailed inspection.

24 Claims, 13 Drawing Sheets

FIG.9
(a)
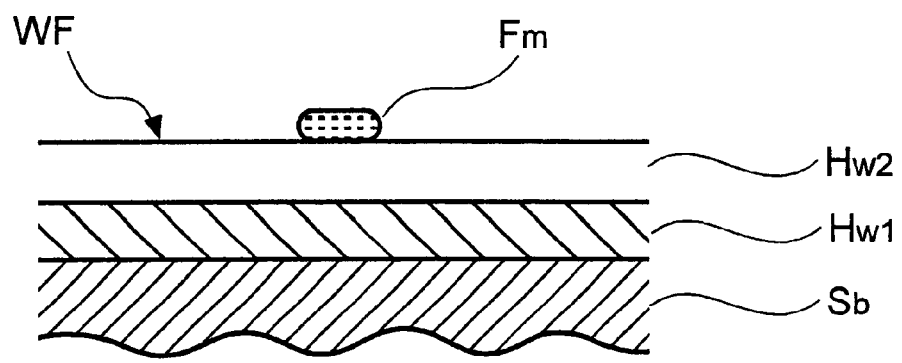
(b)
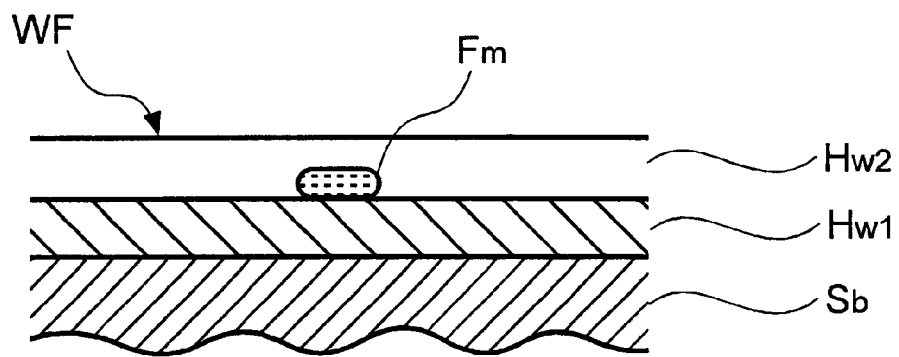

FIG.11
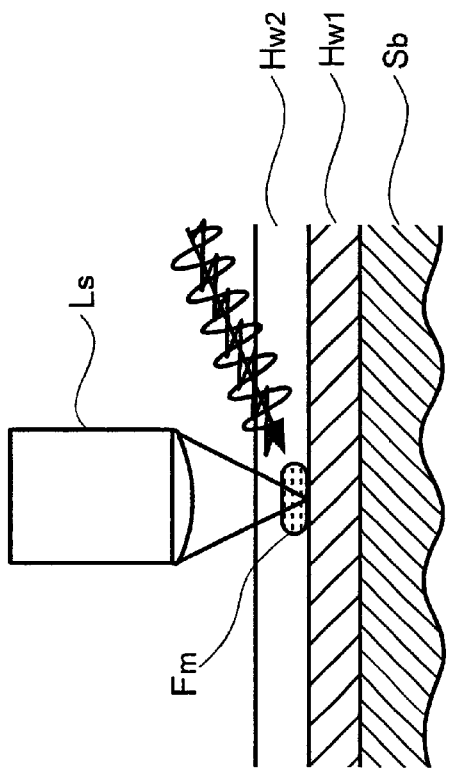
(a)
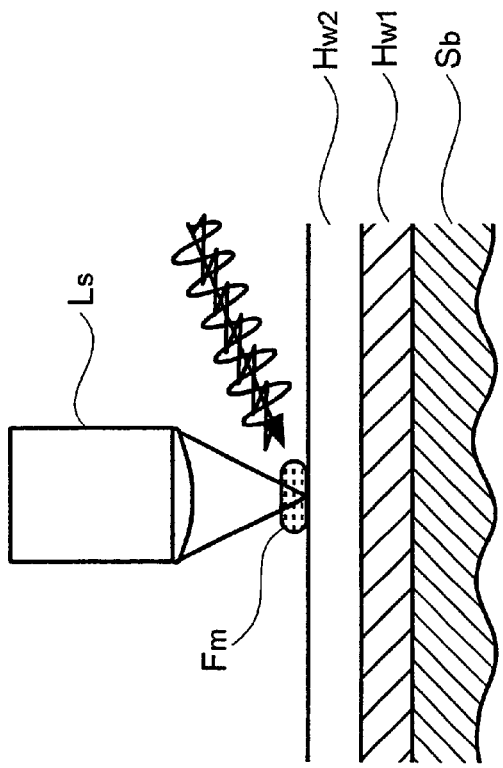
(b)

FIG.12

| Defect inspection settings ||
|---|---|
| Size | 0 [μm]　　1.2 [μm] |
| Concentration sampling | ◉　　5 [%] |
| Delete defects from previous process | ◉ |
| Film | ◉ on film　　○ under film |
| Circuit | ◉ on circuit　　◉ outside of circuit |
| Pattern defect A | ◉ |
| Pattern defect B | ○ |
| Particle A | ◉ |
| Particle B | ◉ |
| Particle C | ○ |

METHOD AND ITS APPARATUS FOR INSPECTING A SPECIMEN

CROSS-REFERENCES TO RELATED APPLICATIONS

This application claims priority from Japanese Patent Application Reference No. 11-264164, filed Sep. 17, 1999.

BACKGROUND OF THE INVENTION

The present invention relates to a method and device for inspecting particles and defects that occur on a specimen such as a semiconductor wafer in a semiconductor production process.

Semiconductor devices are produced by performing a plurality of processes such as exposure, development, etching, and the like on a wafer, which serves as a substrate. A particle inspection device or pattern inspection device is used after predetermined processes out of this plurality of processes in order to inspect the positions and sizes of particles and defects on the wafer. Using an optical microscope or an SEM (scanning electron microscope), magnified images are manually generated for some or all of the particles and defects detected by the inspections. This provides detailed information such as sizes, shapes, and textures (surface patterns), and helps to determine the process in which the particles and defects were generated.

Recent years have seen the development of devices for generating magnified images equipped with ADR (auto defect review), which is a feature for automatically obtaining magnified images of particles and defects based on inspection data from particle inspection devices and pattern inspection devices.

As described above, ADR is performed using inspection data from particle inspection devices and pattern inspection devices. Due to noise and the like, the inspection data from these inspection devices often contains significant amounts of false alarm (e.g., a non-existent defect is reported). Attempting to increase inspection precision will increase the false alarm. In such cases, ADR will obtain a large number of images that do not contain defects, thus resulting in wasted inspection time.

Also, due to differences in the inspection systems, a defect detected by a particle detection device or a pattern inspection device may not be detected by a details inspection device. For example, if the details inspection device is an SEM, particles present under a transparent layer formed on the wafer will not be observable. As with the case above, ADR will result in images where particles and defects cannot be observed or images in which particles and defects are not present, thus resulting in wasted inspection time.

With manual observations, if viewing a particle or defect using a front view image is difficult, the imaging conditions can be adjusted, e.g., by varying the observation angle.

However, with ADR, imaging conditions cannot be changed according to characteristics of particles and impurities. Thus, images that provide the information needed for analysis may not be possible. This will also lead to wasted inspection time.

SUMMARY OF THE INVENTION

The object of the present invention is to eliminate the problems of the conventional technology and to provide an inspection method and device that implements improved efficiency and effectiveness in inspection of details.

The method for inspecting specimens according to the present invention is a method for inspecting defects in the specimen in which detailed inspections performed on defects detected by a defect inspection process are controlled on the basis of information relating to the defects. In the defect inspecting process, position information of defects on the specimen is obtained, and attribute information indicating characteristics of the defects for which the defect position information was acquired is added. In the detailed inspection process, the inspection positions are determined based on the position information and detailed inspection is performed based on the attributes.

The attribute information can include: defect characteristics obtained from relative positioning of defect position information obtained by the defect inspection process; defect attribute information obtained by inspecting defects based on the defect position information using means for optical detection; or comparing defect position information obtained by the defect inspecting process with defect position information obtained from a defect inspecting process from another process.

Furthermore, the attribute information according to the present invention can include information indicating whether or not a defect is on the surface of the specimen or whether or not detailed inspection is to be performed on the defect.

A specimen inspection device according to the present invention includes: means for detecting defects that detects defects on the specimen; means for adding attributes that adds attribute information to the defects; means for storing that stores attribute information; and means for performing detailed inspection that performs detailed inspection of defects based on the attribute information.

Alternatively, the specimen inspection device according to the present invention can include: means for detecting defects that defects defects on a semiconductor wafer that serves as the specimen; means for evaluating that evaluates whether the defects detected by the defect detecting means is on the surface of the semiconductor wafer or below the surface; means for storing that store information relating to coordinates of the defects detected by the defect detecting means and evaluation results from the evaluating means; and mean for outputting that outputs information relating to coordinates of the defects, detected by the defect detecting means and evaluation results from the evaluating means stored in the storing means.

Having the structures described above, the defect inspecting method of the present invention can determine whether or not each defect detected on the specimen should have a detailed inspection performed based on the attributes added to the defect. This allows detailed inspections to be performed reliably only for the defects that require detailed inspections, thus eliminating needless detailed inspections and improving detailed inspection efficiency and reducing the time involved.

Also, according to the present invention, imaging conditions in the detailed inspection can be set up beforehand based on the attributes added to the defects and particles. This allows imaging conditions for detected defects and particles to be varied according to their attributes, thus providing images that can be easily studied based on the type of particle or defect. By setting up conditions suited for image processing, stable image processing results can be provided.

These and other objects, features, and advantages of the invention will be apparent from the following more particular description of preferred embodiments of the invention, as illustrated in the accompanying drawings.

BRIEF DESCRIPTION OF THE DRAWINGS

FIG. 9 shows cross-section drawings of particles on a specimen.

FIG. 11 is a drawing showing another specific example of an optical detector system of the inspection device used to inspect attributes of the particle shown in FIG. 9.

FIG. 12 is a drawing showing a specific example of evaluation conditions for particles and defects on which detailed inspection is to be performed.

DESCRIPTION OF THE SPECIFIC EMBODIMENTS

The following is a description of the embodiments of the present invention, with references to the drawings.

Figure 1:
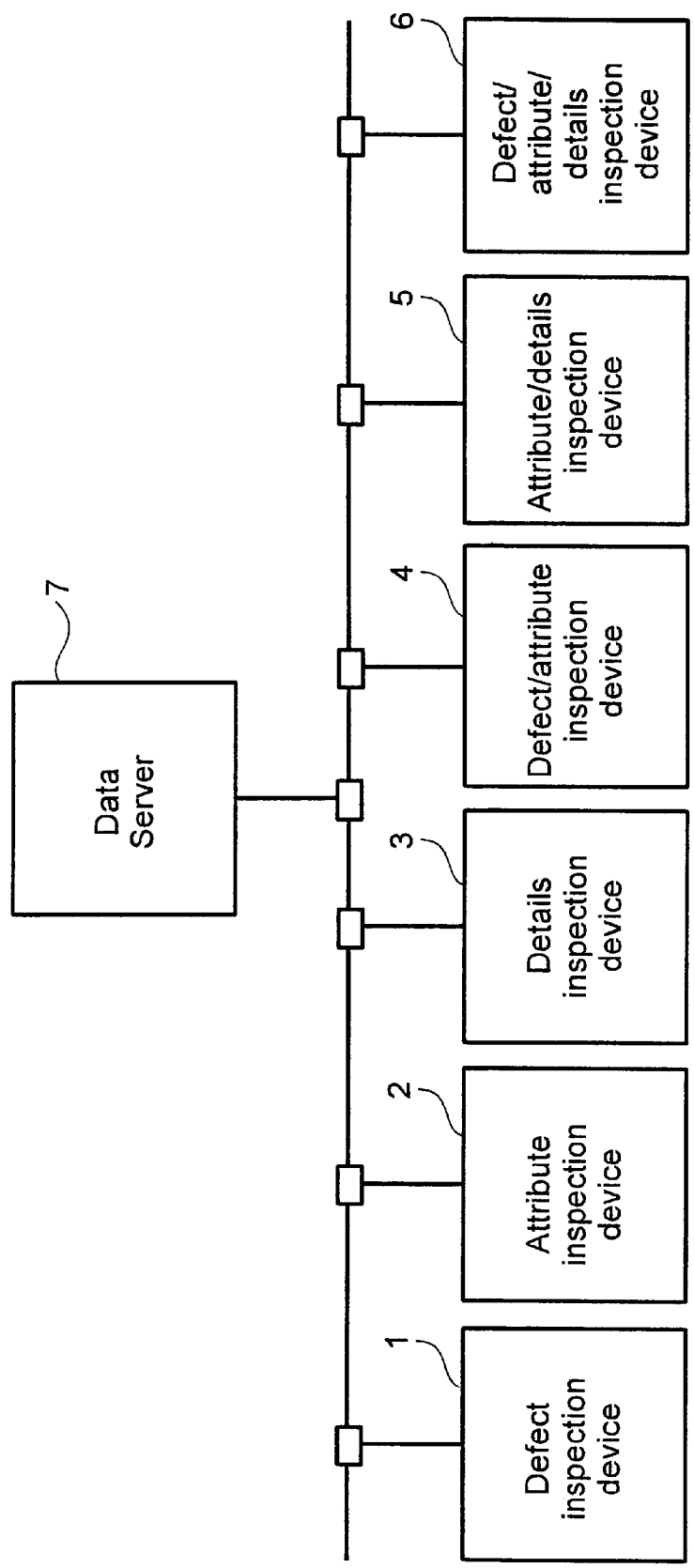
FIG. 1 is a drawing showing the different types of inspection devices used in a specimen inspecting method and device according to the present invention.

FIG. 1 shows the inspection devices used in the specimen inspection device and method according to the present invention. The figure shows a defect inspection device 1 an attributes inspection device 2, a details inspection device 3, a defect/attributes inspection device 4, an attributes/details inspection device 5, a defects/attributes/details inspection device 6, and a data server 7.

The defect inspection device 1 in this figure detects the positions of particles and defects (with certain special exceptions, these will be referred to collectively as defects below) on the semiconductor wafer. For example, an inspection device such as the WI-890 from Hitachi Seisakusho can be used.

The attributes inspection device 2 is an inspection device equipped with means for acquiring inspection information, means for inspecting defect attributes, and means for adding attributes.

The details inspection device 3 is an inspection device equipped with means for evaluating, which determines an inspecting method based on the attributes mentioned above, and means for inspecting details of defects.

The defects/attributes inspection device 4 is an inspection device equipped with means for detecting defects and means for adding attributes of these defects.

The attributes/details inspection device 5 is equipped with means for acquiring inspection information, means for inspecting attributes of defects, means for adding attributes, and means for inspecting details based on these attributes.

The defects/attributes/details inspection device 6 is equipped with means for inspecting defect positions, means for inspecting attributes of defects based on this position information, means for adding attributes adding these defect attributes, and means for inspecting details based on these attributes.

The data server 7 is a data server that manages the inspection data obtained by inspection devices 1–6.

These inspection devices 1–6 are connected to the server 7 by a network, and the data relating to defects obtained by these inspection devices are sent through the network to the data server 7, where this information is managed. Not all of the inspection devices 1–6 are used, however. Semiconductor wafers are inspected by a combination of one or more of these inspection devices. Based on these combinations, the following is a description of the method and device for inspecting specimens according to the present invention.

In the first embodiment, the inspection devices 1–3 from FIG. 1 are combined. The attributes inspection device 2, which is equipped with an optical microscope and an imaging device, obtains images using data representing the positions on the semiconductor wafer of defects detected by the defect detecting device 1 (this data will be referred to as defect position data). The resulting images are analyzed to determine the attributes of the defects, and defects are selected based on these attributes. Only the selected defects are inspected by the details inspection device 3.

Figure 2:
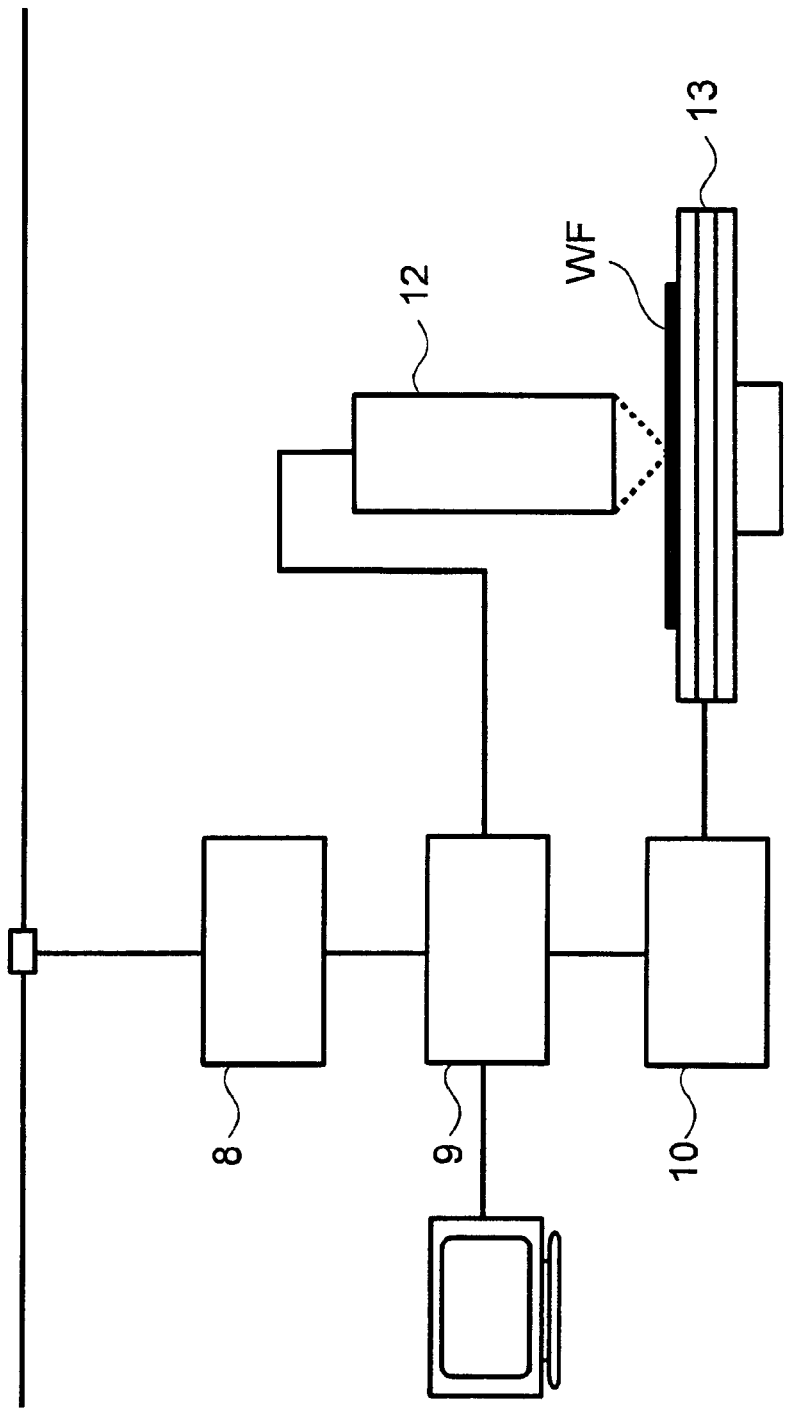
FIG. 2 is a drawing showing the architecture of one example of the attribute inspection device from FIG. 1 used in the first embodiment of the specimen inspecting method and device according to the present invention.

FIG. 2 is a drawing showing the architecture of a specific example of the attributes inspection device 2 from FIG. 1. The figure shows an information input/output device 8, a computer 9, a control device 10, a monitor 11, an imaging device 12, an XYZ stage 13, and a semiconductor wafer WF, which serves as the inspected specimen.

In this figure, the inspected specimen, semiconductor wafer WF, is secured to the XYZ stage 13. The XYZ stage 13 can be displaced in the X, Y, and Z directions by the control device 10 based on control signals from the computer 9.

The imaging device 12 is equipped with an optical microscope. This optical microscope is used to generate a magnified image of the semiconductor wafer WF. By controlling the XYZ stage 13, different positions on the semiconductor wafer WF can be magnified and observed. The semiconductor wafer WF has been inspected for defects using the defects inspection device 1 (FIG. 1), and the defect position data obtained through this inspection is stored in the data server 7 (FIG. 1). When the semiconductor wafer WF is inspected using the attributes inspection device 2, the computer 9 of FIG. 2 acquires the defect position data obtained from the semiconductor wafer WF from the data server 7 via the information input/output device 8. Based on this defect position data, control signals are sent to the control circuit 10, and the XYZ stage 13 is positioned to allow the imaging device 12 to examine the positions of the defects or the particles on the semiconductor wafer WF. The information input/output device 8 can be contained in the computer 9.

The computer 9 acquires an image obtained by the imaging device 12 and displays it on the monitor 11. This image is analyzed and defect attributes information (hereinafter referred to as attributes information) is added to the defect position data, and this is stored in the data server 7 via the information input/output device 8.

These attributes serve as the basis for determining whether or not a defect should be inspected by the subsequent inspection performed with the details inspection device 3 (FIG. 1). As a result of image analysis performed by the computer 10, if a defect has attributes where the process in which the defect was generated or the cause of the defect is clear, or if the defect has attributes that cannot be measured by the details inspection device 3, the defect is not inspected by the details inspection device 3.

Attributes can include coloration of the defect (e.g., color differences such as white/black), size of the defect, shape of the defect, and the like. These attributes allow defects for which the cause can be determined to be distinguished from defects for which the cause cannot be determined. For example, it may be possible to determine the cause of defects that appear white in the image analysis but not possible for defects that appear black. Also, adequate analysis may not be possible for small defects due to the low magnification and the low resolution of the optical microscope, thus requiring another inspection by the details inspection device 3 using a high-resolution SEM or the like. In this manner, the attributes information is used to determine whether or not a defect is to be re-inspected using the details inspection device 3.

In addition to attributes obtained through image analysis, attributes obtained with other methods can also be included in the attributes added to the defect. For example, when a large number of defects are concentrated, it may not be clear what the cause is so that further inspection using the details inspection device 3 is necessary. Thus, whether or not a large number of defects are concentrated can be an attribute of these defects.

Also, a large number of defects can be arranged along a single curve such as in the case of a scratch. This can also be an attribute. Furthermore, inspection results of the inspected semiconductor wafer from the current inspection process with the defect inspection device 1 can be compared with the inspection results from a previous inspection process that used a defect inspection device. This can determine whether a defect detected in the current inspecting process was newly generated or whether the defect was already present in a previous production process. This can also be an attribute. Defects already present in a previous production process does not require inspection by the details inspection device 3.

Furthermore, attributes information can also be information based on the inspection results from the attributes inspection device 2 such as "inspection by details inspection device 3 required" or "inspection by details inspection device 3 not required".

Figure 3:
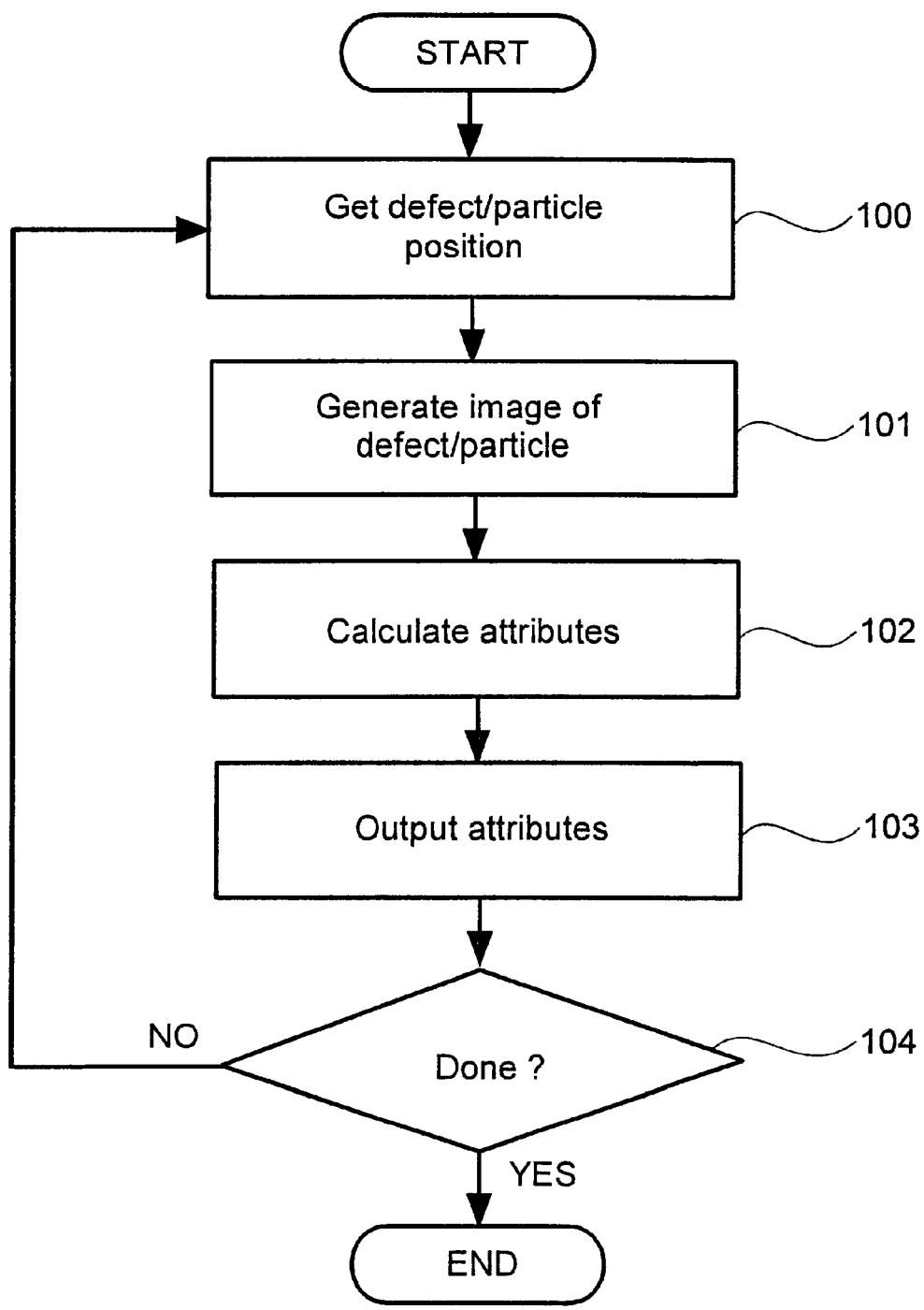
FIG. 3 is a flowchart showing the inspection process in the attributes inspection device shown in FIG. 2.

FIG. 3 is a flowchart showing the inspection operations performed by the attributes inspection device 2 from FIG. 2.

In FIG. 2 and FIG. 3, the computer 9 first queries the data server 7 for data regarding the inspected semiconductor wafer WF mounted on the XYZ stage 13, and obtains defect position data for the semiconductor wafer WF (step 100). Using this defect position data, the control device 10 controls the XYZ stage 13 so that a particle or defect enters the field of view of the optical microscope in the imaging device 12. The particle or defect is magnified by the optical microscope and the imaging device 12 generates an image (step 101).

Next, the magnified image of the particle or defect is displayed on the monitor 11, and the particle or defect in this magnified image is analyzed. This analysis involves categorization using a categorization engine such as fuzzy inference or neural networks based on training data prepared beforehand manually. The categorization results are added to the defect as attributes (step 102). These added attributes are output as attribute information to the data server 7 (FIG. 1) via the information input/output device 8, where the data server 7 manages it along with the corresponding defect position data (step 103). These inspection operations are performed for each of the defects detected by the defects inspection device 1 (FIG. 1) (step 104).

Figure 4:
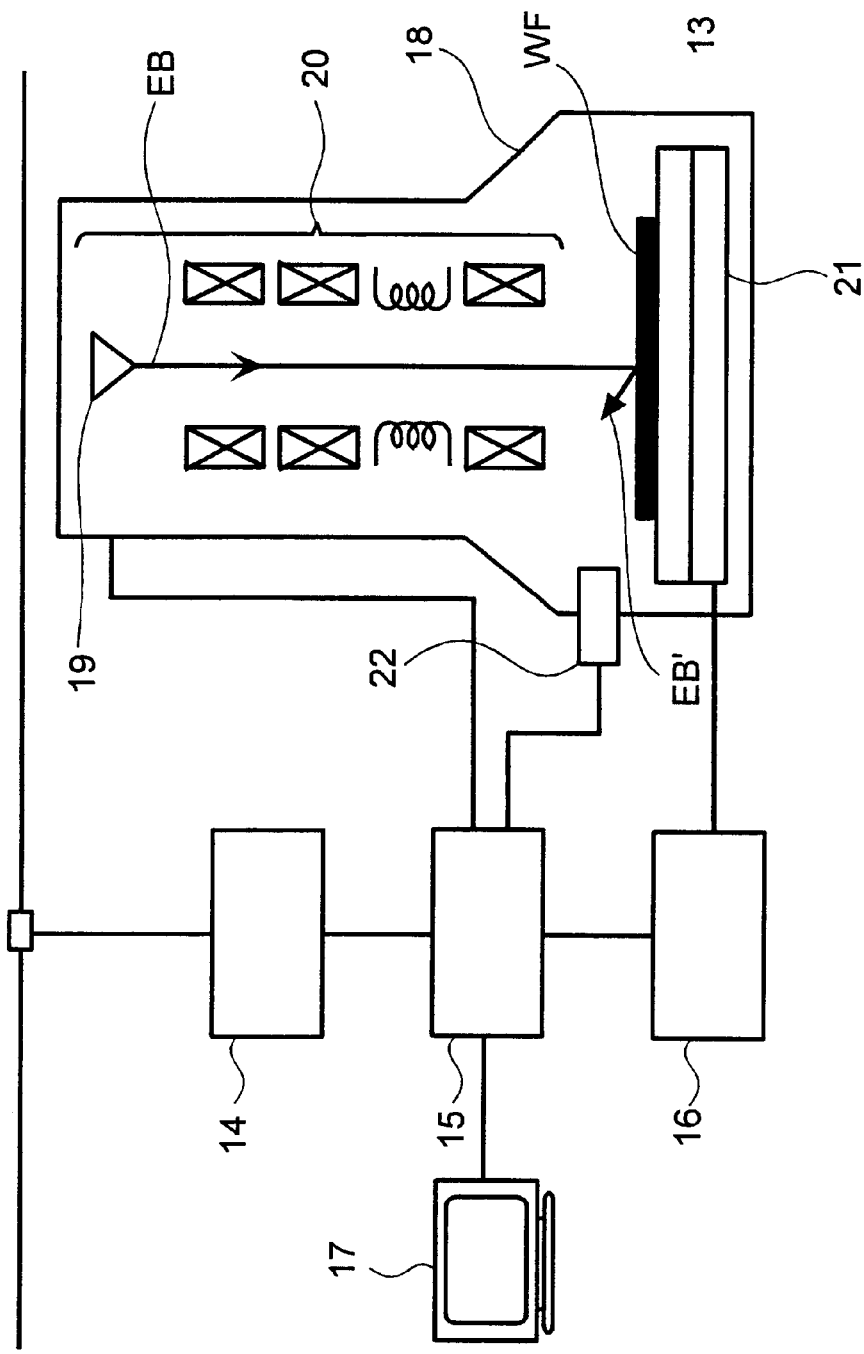
FIG. 4 is a drawing showing the architecture of one example of the details inspection device from FIG. 1 used in the first embodiment of the specimen inspecting method and device according to the present invention.

FIG. 4 is a drawing showing the architecture of a specific example of the details inspection device 3 from FIG. 1. The figure shows an information input/output device 14, a computer 15, a control device 16, a monitor 17, an imaging device 18 that uses an SEM (scanning electron microscope), an electron beam source 19, an electro optical system 20, an XY stage 21, a secondary electron detector 22, an electron beam EB, and a secondary electron EB'. Also shown is the semiconductor wafer WF, which was inspected by the attributes inspection device 2 shown in FIG. 2.

Of the defects inspected by the attributes inspection device 2 from FIG. 2, this details inspection device 3 performs a detailed inspection of only the defects determined to require inspection based on the attributes. In this case, defect details can be inspected with a high magnification due to the use of an SEM.

In the figure, the computer 15 serves as evaluating means evaluating whether or not detailed inspection of a defect is needed and evaluating inspection condition settings based on the attributes obtained by the attributes inspection device 2 from FIG. 2. Based on the evaluations provided by evaluating means, the imaging device 18 serves as inspecting means inspecting the details of the defect and outputs a magnified image.

The inspected semiconductor wafer WF is secured to the XY stage in the imaging device 18. Using the information input/output device 14, the computer 15 acquires from the data server 7 (FIG. 1) defect position data and attributes information for the defects detected by the defect detecting device 1 (FIG. 1) for the semiconductor wafer WF secured to the XY stage 21. For each defect having defect position data, the attributes information is used to determine whether the defect or particle should be inspected. For each defect that is to be inspected, control signals based on the corresponding defect position data are sent to the control device 16, and the control device 16 positions the XY stage 21 to allow the imaging device 18 to inspect the defect. Also, the attributes of the defect to be inspected are used to determine inspection conditions such as imaging conditions for the defect, and a settings control signal is sent to the imaging device 18 in order to set up these inspection conditions.

In the imaging device 18, the electron beam generator 19 and the electro optical system 20 are controlled to focus and deflect the electron beam EB so that it scans the region of the inspected defect on the semiconductor wafer WF. In this case, the scanning region can be varied according to inspection conditions. For example, if an inspected defect is a single defect or particle, the electron beam EB would scan the region containing it. If the inspected defect is a concentration of many defects, the electron beam EB would scan the region containing these defects.

The application of the electron beam EB results in the generation of the secondary electron EB' from the position of the defect on the semiconductor wafer WF. By detecting this with the secondary electron detector 22, a magnified image (referred to as a SEM image) of the particle or defect on the semiconductor wafer WF is obtained. This SEM image is captured by the computer 15 and displayed on the monitor 17 as well as being sent via the information input/output device 14 to the data server 7 (FIG. 1), where it is stored. The user can observe the details of the defect using the monitor screen, thereby determining the cause of the defect and the like. Of course, it would also be possible to do these things by having the computer 15 analyze the SEM image and send the results to the data server 7 (FIG. 1) via the information input/output device 14 as new attribute information.

The imaging device 18 can also be equipped with an X-ray analysis device that analyzes the material composition of the defect depending on the attributes. The magnified image resulting from this analysis would be captured by the computer 15, displayed on the monitor 17, and stored in the data server 7. Furthermore, the analysis results can be stored in the data server 7 as new attributes.

The defect position data and the various types of attributes data described above that are stored in the data server 7 can also be output to a separate output device such as a monitor or a printer.

Figure 5:
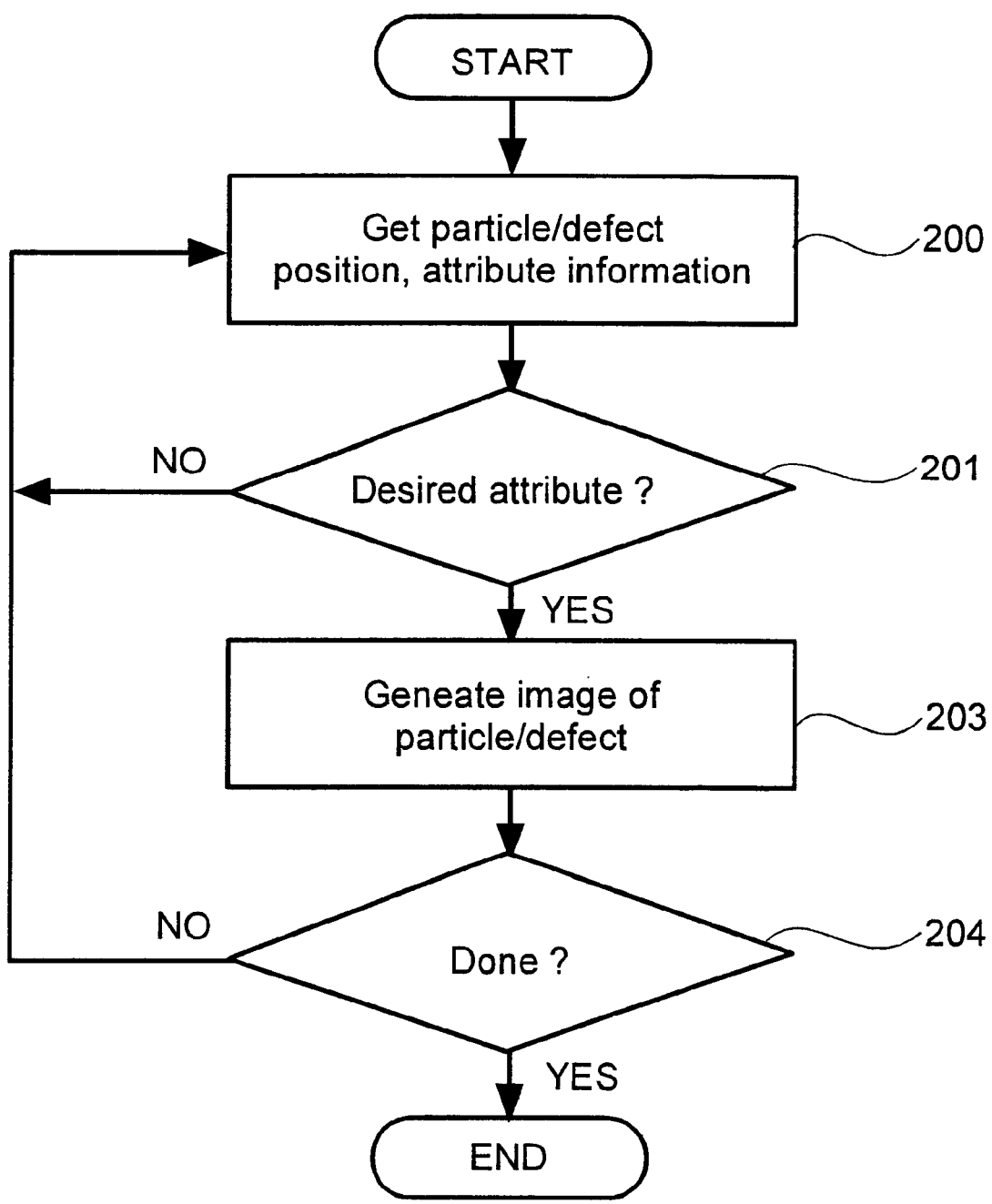
FIG. 5 is a flowchart showing the inspection process performed by the detailed inspection device shown in FIG. 4.

FIG. 5 is a flowchart showing the inspection operations performed by the details inspection device 3 shown in FIG. 4.

In the figure, the computer 15 first queries the data server 7 regarding the semiconductor wafer WF being inspected in order to acquire defect position data for a defect on the semiconductor wafer WF obtained by the defects inspection device 1 (FIG. 1) as well as attributes information added by the attributes inspection device 2 (FIG. 1) (step 200). If the attributes information indicates that the particle or defect should not be inspected by the details inspection device 3 (step 201), the data server 7 is queried to obtain the next defect position data and the corresponding attributes information (step 200). This particle or defect is evaluated to see if it should be inspected (step 201). If it is a particle or defect that is to be inspected (step 201), the imaging device 18 is operated as described above to acquire an SEM image (step 203). These operations are performed for all defects detected on the semiconductor wafer WF mounted on the XY stage 21 (step 204).

As described above, the first embodiment uses the defects inspection device 1, the attributes inspection device 2, and the details inspection device 3 to select defects for inspection by the details inspection device 3 based on attributes information obtained by the attributes inspection device 2. The attributes inspection device 2 is advantageous because it uses an optical microscope for inspection, and defects can be inspected quickly. However, magnification and resolution are low, preventing precise inspection. In particular, very fine defects are difficult to inspect. In contrast, SEMs and X-ray analysis devices require time to inspect each individual defect, making inspection time consuming. However, images with high magnification and resolution are provided, allowing accurate analysis. Also, with SEMs and X-ray analysis devices, certain defects cannot be inspected due to their being inside a layer or the like.

In the first embodiment, the characteristics of the attribute inspection device 2 equipped with an optical microscope and the characteristics of the details inspection device 3 equipped with an SEM or an X-ray analysis device are both used. Defects are inspected by only the attributes inspection device 2 if an inspection with an optical microscope allows the cause to be determined or if a defect is a type that cannot be inspected by the details inspection device 3. If a defect can be inspected by the details inspection device 3 and requires detailed inspection, the defect is inspected with details inspection device 3. Whether or not a defect should be inspected by the details inspection device 3 is determined by attributes obtained from the analysis results from the attributes inspection device 2.

Thus, in the first embodiment, defects requiring detailed inspection are inspected using the details inspection device 3, and all other defects are inspected using the attributes inspection device 2, which is less time consuming. This allows elimination of unneeded detailed inspections, thus greatly reducing inspection time while providing adequate inspection results. As a result, both the inspections are more efficient and effective.

In the second embodiment, the defects/attributes inspection device 4 and the details inspection device 3 from FIG. 1 are combined. The defects/attributes inspection device 4 is equipped with the defects inspection device 1 and the attributes inspection device 2 from FIG. 1. Based on the attributes obtained by the defects/attributes inspection device 4, the details inspection device 3 selects defects to be inspected and performs detailed inspections on these defects.

Figure 6:
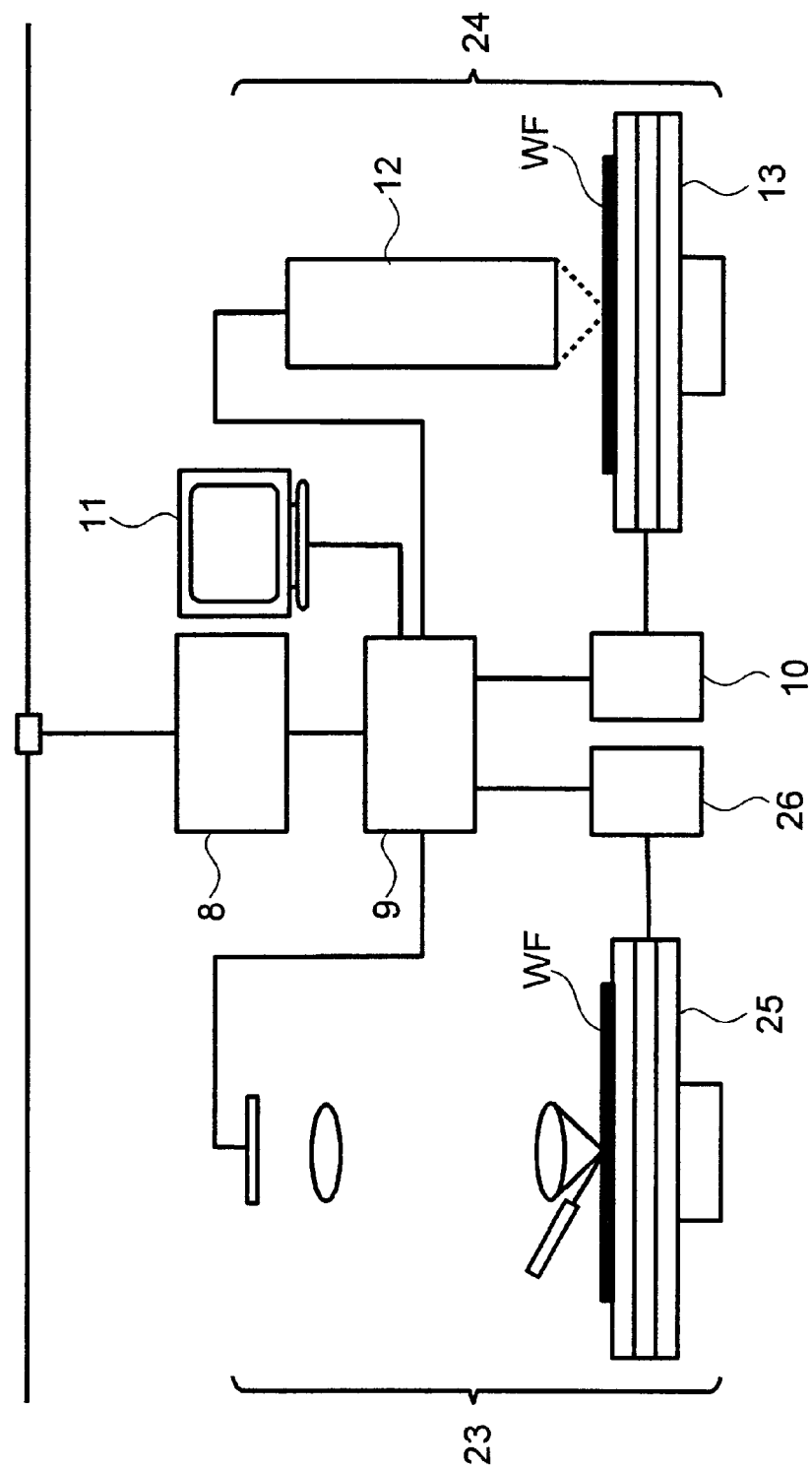
FIG. 6 is a drawing showing the architecture of a specific example of the defect/attributes inspection device from FIG. 1 used in the second embodiment of the method and device for inspecting specimens according to the present invention.

FIG. 6 shows the architecture of a specific example of the defects/attributes inspection device 4. The figure shows a defects inspecting system 23, an attributes inspecting system 24, an XYZ stage 25, and a control device 26. Elements corresponding to those from FIG. 2 are assigned the same numerals, and overlapping descriptions will be omitted.

In the figure, the defects/attributes inspection device 4 includes the defect inspecting system 23, which inspects defect positions as in the defects inspection device 1 from FIG. 1, and the attributes inspecting system 24, which inspects the attributes of defects based on the position data obtained by the defect inspecting system 23 as in the attributes inspection device 2 from FIG. 2.

The semiconductor wafer WF to be inspected is first mounted on the XYZ stage 25 of the defect inspecting system 23. Then, the computer 9 controls the inspection of defects on the semiconductor wafer WF. The defect inspecting system 23 is controlled by the computer 9. In response to inspection position instructions from the computer 9, the control device 26 moves the XYZ stage 25 in the X and Y directions so that the entire area of the semiconductor wafer WF can be inspected. The computer 9 keeps track of the inspection positions of the semiconductor wafer WF. As defects are detected in the inspection performed by the defect inspecting system 23, the inspection positions are recorded as defect position data. In this manner, the computer 9 acquires the defect position data for the semiconductor wafer WF. The defect position data acquired in this manner can be stored in the data server 7 via the information input/output device 8 (FIG. 1).

When the defect inspecting system 23 completes the defect inspection operation for the semiconductor wafer WF, the semiconductor wafer WF is moved to the attributes inspecting system 24, where it is mounted on the XYZ stage 13. Based on the acquired defect position data, the computer 9 controls the attributes inspecting system 24 to perform operations corresponding to those performed by the attributes inspection device 2, described with reference to FIG. 2. As described above, attributes are detected for each defect position represented in the defect position data. The attribute information detected in this manner is added to the defect position data, and is stored in the data server 7 (FIG. 1) via the information input/output device 8. Of course, the defect position data and the attributes information obtained in this manner can be displayed on the monitor 11 or can be output to a printer (not shown in the figures).

Next, the details inspection device 3 (FIG. 4) acquires the defect position data and the attributes information from the data server 7. The attributes information is used to select defects for detailed inspections. Detailed inspections are then performed for these selected defects.

The second embodiment provides similar advantages as the first embodiment. In addition, since the defect inspecting system 23 and the attributes inspecting system 24 are integrally disposed, defect inspection and attributes inspection can be performed as a continuous operation. This reduces the time required in inspecting each defect.

In the above description, the semiconductor wafer WF is transferred from the defect inspecting system 23 to the attributes inspecting system 24, but it would also be possible to use the same XYZ stage mounting the semiconductor wafer WF for both the defect inspecting system 23 and the attributes inspecting system 24. When the inspection performed by the defect inspecting system 23 is completed, the XYZ stage on which the semiconductor wafer WF is mounted would then be moved to the attributes inspecting system 24. Of course, in this case, there would be no need to provide the control devices 26, 10 for the inspecting systems 23, 24. A common control device can be used to provide appropriate control over the inspecting systems 23, 24, thus allowing the device to be simplified.

In the third embodiment, the attributes/details inspection device 5 and the defects inspection device 1 from FIG. 1 are combined. The attributes/details inspection device 5 is equipped with the attributes inspection device 2 and the details inspection device 3 from FIG. 1.

Figure 7:
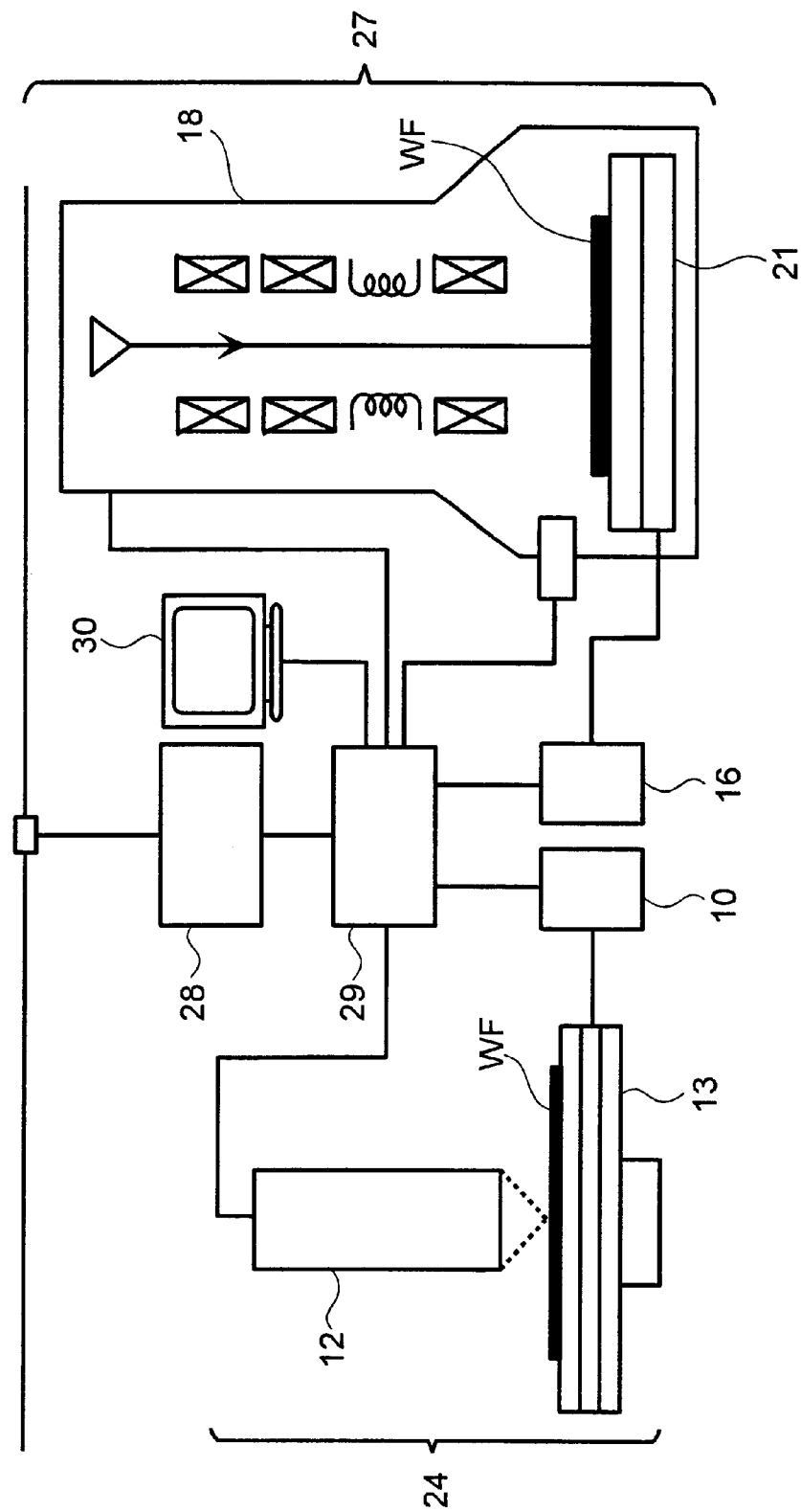
FIG. 7 is a drawing showing the architecture of a specific example of the attributes/details inspection device from FIG. 1 used in the third embodiment of the method and device for inspecting specimens according to the present invention.

FIG. 7 is a drawing showing the architecture of a specific example of the attributes/details inspection device 5. The figure shows a details inspecting system 27, an information input/output device 28, a computer 29, and a monitor 30. Elements corresponding to those from FIG. 4 and FIG. 6 are assigned like numerals, and overlapping descriptions are omitted.

The effects/attributes inspection device 4 from FIG. 7 is equipped with the attributes inspecting system 24 described with reference to FIG. 6 and a details inspecting system 27, similar to the details inspection device 3 shown in FIG. 4, performing detailed inspections on defects selected on the basis of attributes information obtained by the attributes inspecting system 24. The information input/output device 28, the computer 29, and the monitor 30 are shared between the attributes inspecting system 24 and the details inspecting system 27. For the attributes inspecting system 24, the information input/output device 28, the computer 29, and the monitor 30 correspond respectively to the information input/output device 8, the computer 9, and the monitor 11 from FIG. 2. For the details inspecting system 27, the computer 29, and the monitor 30 correspond respectively to the information input/output device 14, the computer 15, and the monitor 17 from FIG. 4.

The semiconductor wafer WF to be inspected first undergoes a defect inspection by the defects inspection device 1 from FIG. 1, and the resulting defect position data is stored in the data server 7.

When defect inspection by the defects inspection device 1 is completed, the semiconductor wafer WF is mounted on the XYZ stage 13 of the attributes inspecting system 24. At the same time, the computer 29 acquires the defect position data for the semiconductor wafer WF from the data server 7 (FIG. 1) via the information input/output device 28. Based on this defect position data, the defects detected by the defects inspection device 1 are inspected to determine attribute information, as described with reference to FIG. 2. This attribute information is stored along with the defect position data in the computer 29, but can also be stored in the data server (FIG. 1) via the information input/output device 28.

When attribute inspection by the attributes inspecting system 24 is completed, the semiconductor wafer WF is next transferred from the attributes inspecting system 24 to the details inspecting system 27 and is mounted on the XYZ stage 21. As with the details inspection device 3 described with reference to FIG. 4, this details inspecting system 27 is controlled by the computer 29 and performs detailed inspections on defects selected based on attributes information obtained by the attributes inspecting system 24. Alternatively, imaging conditions can be varied for each defect according to the attributes information, and the resulting magnified images can be analyzed to provide inspection of details. Also, the details inspecting system 27 can be equipped with means for performing X-ray analysis, and X-ray analysis can be performed on defects as described above. Of course, magnified images or analysis results obtained in these ways can be displayed on the monitor 30 or output to a printer (not shown in the figures).

The magnified images or analysis results obtained in these ways are stored in the data server (FIG. 1) via the information input/output device 28 along with the defect position data and attributes information described above.

The third embodiment as described above provides similar advantages as the first embodiment. Furthermore, since the attributes inspecting system 24 and the details inspecting system 27 are integrally disposed, the attributes inspection and the details inspection can be performed as a continuous operation, thus reducing the amount of time required for inspecting each defect.

In the above description, the semiconductor wafer WF is transferred from the attributes inspecting system 24 to the details inspecting system 27. However, an XYZ stage for mounting the semiconductor wafer WF can be shared between the attributes inspecting system 24 and the details inspecting system 27. When inspection by the attributes inspecting system 24 is completed, the XYZ stage on which the semiconductor wafer WF is mounted would be moved to the details inspecting system 27. Of course, in this case, separate control devices 10, 16 would not be required for the inspecting systems 24, 27. A shared control device can be used to control the inspecting systems 24, 27 separately, thus simplifying the device.

The fourth embodiment consists of only the defects/attributes/details inspection device 6 from FIG. 1. The defects/attributes/details inspection device 6 is equipped with the defects inspection device 1, the attributes inspection device 2, and the details inspection device 3 from FIG. 1.

Figure 8:
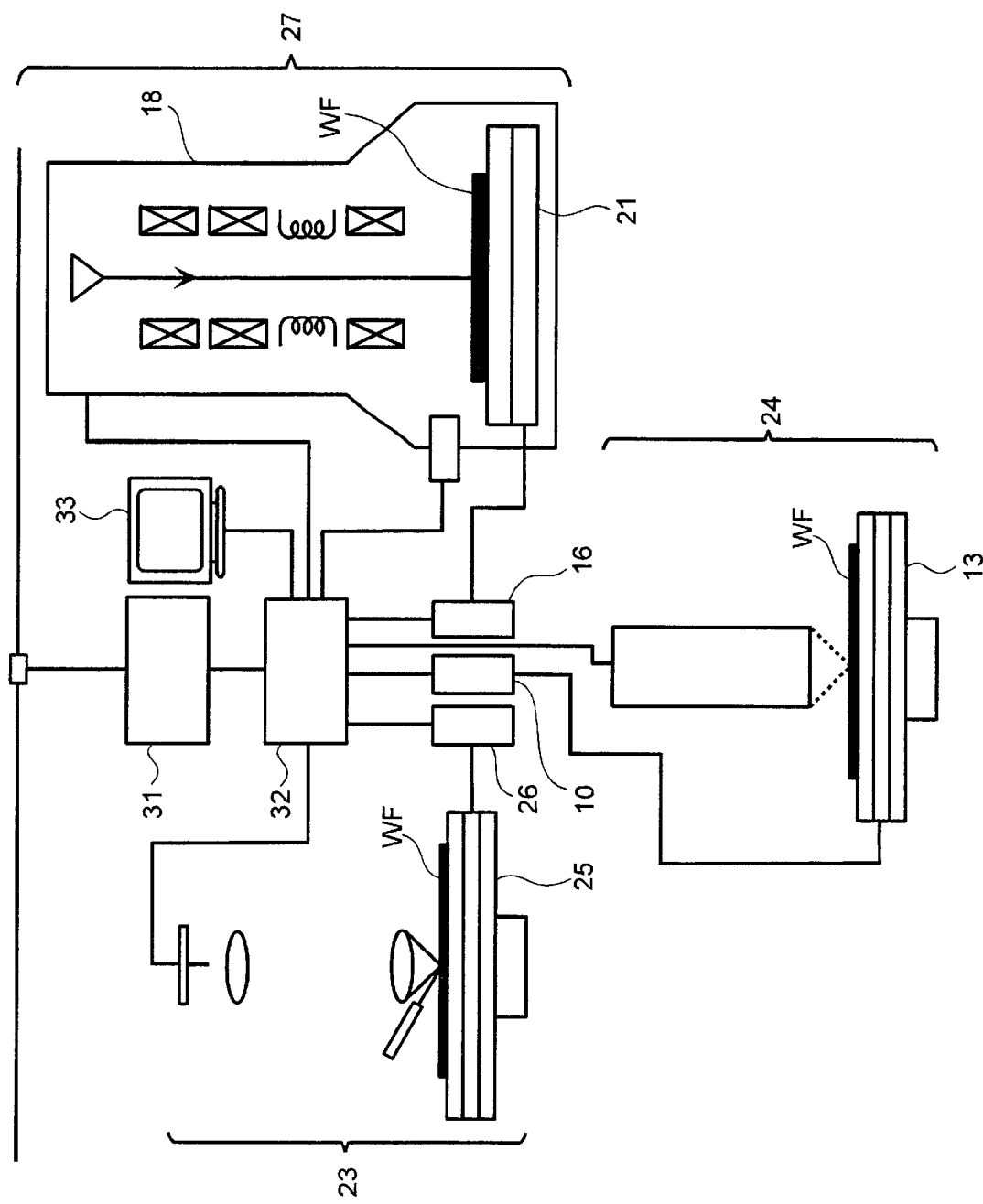
FIG. 8 is a drawing showing the architecture of a specific example of the defects/attributes/details inspection device from FIG. 1 used in the fourth embodiment of the method and device for inspecting specimens according to the present invention.

FIG. 8 is a drawing showing the architecture of a specific example of the defects/attributes/details inspection device 6. The figure shows an information input/output device 31, a computer 32, and a monitor 33. Elements corresponding to elements described with reference to previous figures are assigned the same numerals and overlapping descriptions are omitted.

In this figure, the defects/attributes inspection device 4 is equipped with the defects/attributes inspection device 4 shown in FIG. 6 with the addition of the details inspecting system 27 shown in FIG. 7. The input/output device 31, the computer 32, and the monitor 33 are shared with the defect inspecting system 23, the attribute inspecting system 24, and the details inspecting system 27.

The semiconductor wafer WF to be inspected is first mounted on the XYZ stage 25 of the defect inspecting system 23. As described above with reference to FIG. 6, defect inspection is performed on the semiconductor wafer WF, and the resulting defect position data is stored in the computer 32. The defect position data can also be stored in the data server 7 (FIG. 1) via the information input/output device 31.

When the inspection performed by the defect inspecting system 23 is completed, the semiconductor wafer WF is transferred to the attributes inspecting system 24 and is mounted on the XYZ stage 13 thereof. As described with reference to FIG. 6, the attributes inspecting system 24 uses the defect position data stored in the computer 32 to inspect the defects detected by the defect inspecting system 23 and determine the attributes. The attributes information is stored in the computer 29 along with the defect position data. It would also be possible to have the data stored in the data server (FIG. 1) via the information input/output device 31. The attributes information may also be displayed along with the defect position data on the monitor 33.

When attributes inspection by the attributes inspecting system 24 is completed, the semiconductor wafer WF is transferred from the attributes inspecting system 24 to the details inspecting system 27 and is mounted on the XYZ stage 21. As described with reference to FIG. 7, the details inspecting system 27 performs detailed inspections on defects selected by attributes information obtained by the attributes inspecting system 24. Alternatively, the imaging conditions for each defect can be changed based on the attributes to obtain magnified images, and these can be analyzed for detailed inspection. It would also be possible to have the details inspecting system 27 equipped with means for performing X-ray analysis and X-ray analysis can be performed on the defects as described above. Of course, the magnified images or analysis results obtained with these methods can be displayed on the monitor 33 or can be output to a printer (not shown in the figures).

The magnified images or analysis results obtained with these methods are stored along with the defect position data and attributes information described above in the data server 7 (FIG. 1) via the information input/output device 31.

The fourth embodiment as described above provides similar advantages as the first embodiment. Furthermore, since the defect inspecting system 23, the attributes inspecting system 24, and the details inspecting system 27 are integrally disposed, the operations from the defect inspection through the detailed inspection can be performed as a continuous operation. This reduces the time required for inspecting each defect.

In the description above, the semiconductor wafer WF is transferred from the defect inspecting system 23 to the attributes inspecting system 24, and then from the attributes inspecting system 24 to the details inspecting system 27. However, it would be possible to share an XYZ stage for mounting the semiconductor wafer WF between the defect inspecting system 23 and the attributes inspecting system 24 and the details inspecting system 27. This XYZ stage would be moved between the inspecting systems. Of course, in this case there would be no need to provide separate control devices 26, 10, 16 for the inspecting systems 23, 24, 27. A shared control device can be used for the inspecting systems 23, 24, 27 to provide appropriate control. This provides a simplified device.

The following is a description of a specific example regarding the attributes of a particle generated in a production process for the semiconductor wafer WF.

FIG. 9 is a vertical cross-section drawing of the semiconductor wafer WF during a production process. The figure shows a particle Fm, a silicon wafer Sb serving as a substrate, and layers Hw1, Hw2, which are layers for circuits and the like.

FIGS. 9(a), (b) show states where the processes for forming the layers Hw1, Hw2 have been performed. In FIG. 9(a), the defect Fm is present on the transparent oxide film layer Hw2, i.e., on the surface of the wafer. In FIG. 9(b), the particle Fm is interposed between the layers Hw1, Hw2, i.e., in an inner layer. The defect Fm as shown in FIG. 9(a) can obviously be detected by an optical microscope, as well as by SEMs and X-ray analysis devices. If the particle is in an inner layer, as shown in FIG. 9(b), an optical microscope will be able to detect the particle but SEMs and X-ray analysis devices will not. Thus, an attribute for the particle Fm can be assigned in terms of whether the particle Fm is on the wafer surface or under the wafer surface. This attribute allows the particles Fm under the surface to be eliminated from detailed inspections using SEMs and X-ray analysis devices, thus making the detailed inspections more efficient.

Rather than having the inspection of the particle Fm provide an attribute indicating whether the particle Fm is on the wafer surface or under it, it would also be possible to have the attribute indicate whether a detailed inspection is to be performed for the particle, i.e., whether a detailed inspection is necessary.

Also, it would also be able to selectively change imaging conditions for particles under the surface by perspective observation, thus providing an image that allows easy observation of bumps in patterns indicating particles.

Determination of whether a defect is on the wafer surface or under the surface is made based on analysis of the optical microscope image. For example, if a particle is under the surface its outline will be less sharp compared to a particle on the wafer surface. A determination is made based on the sharpness of the outline. Also, the color of a defect under the surface will tend to be different compared to a defect on the wafer surface. Thus, a determination can be made by analyzing the color in the region of the defect.

Figure 10:
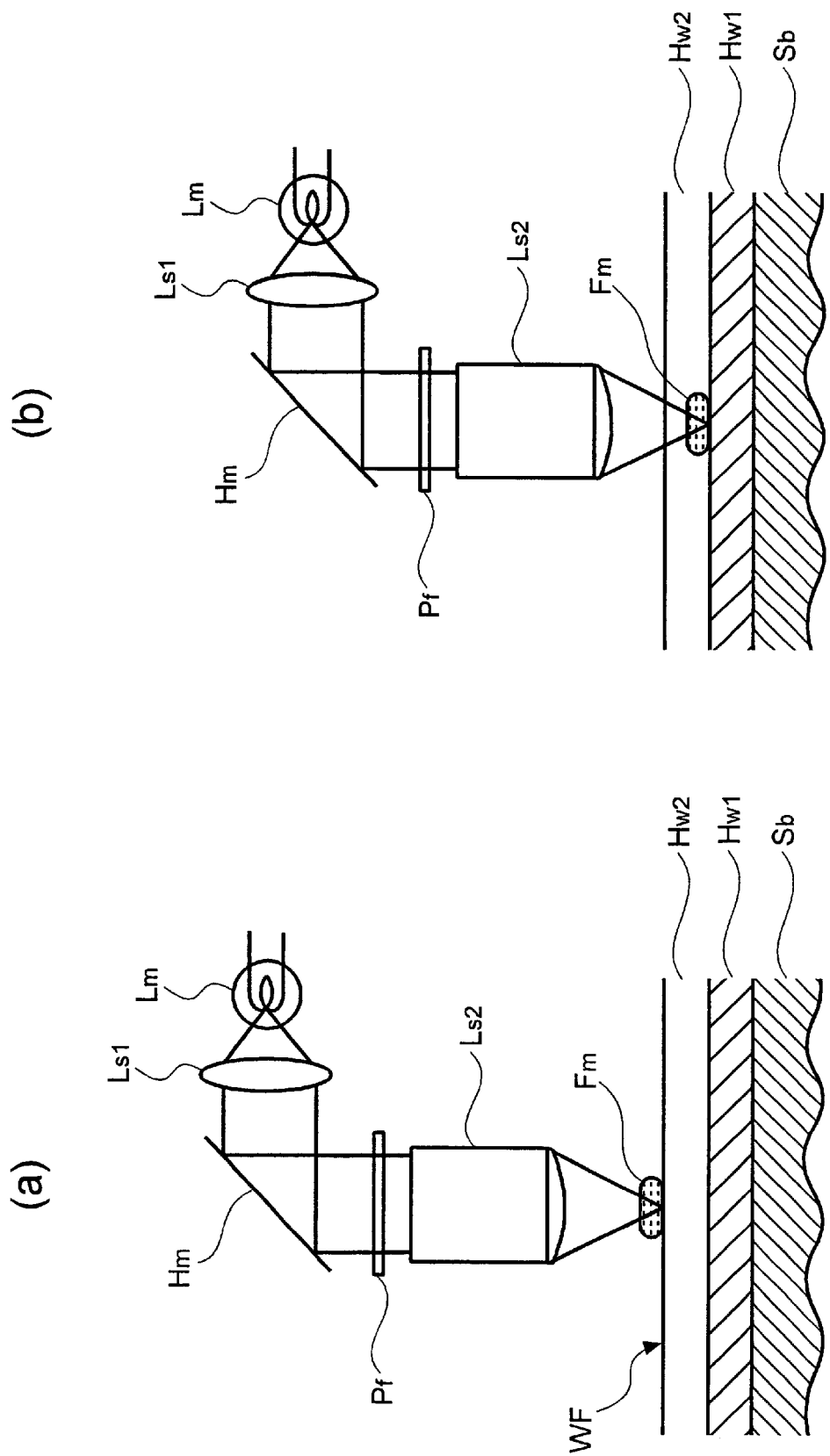
FIG. 10 is a drawing showing a specific example of an optical detector system of the inspection device used to inspect attributes of the particle shown in FIG. 9.

In addition to an optical microscope, a dedicated detection system for evaluating attributes can be used in the imaging device 12 (FIG. 2) of the attributes inspection device 2. For example, FIG. 10 shows a structure of a dedicated detection system that provides an attribute indicating whether a defect is on the wafer surface or under the surface. The figure shows a light source Lm, a collimator LS1, a focus lens LS2, a half mirror Hm, and a polarizing plate Pf. Elements corresponding to elements from FIG. 9 are assigned like numerals.

In this figure, the detection system is formed from: the light source Lm; the collimator LS1, which converts the light beamed from the light source Lm to parallel rays of light; the half mirror Hm that reflects the parallel rays of light; the focus lens LS2 that focuses the parallel rays of light reflected from the half mirror Hm onto the object. The object is thus illuminated by a bright field illumination. A polarizing plate is placed in the optical path, e.g., between the half mirror Hm and the focus lens LS2, so that only S polarized light is passed through. This can also be replaced with an ND filter (Neutral Density Filter) that provides equivalent light attenuation. The reflected light from the object passes through the focus lens LS2, the polarizing plate Pf or the ND filter, and the half mirror Hm, and is detected by an optical detector (not shown in the figure).

If a particle Fm is present at the position where the light is focused, the irregular reflection at the surface of the particle will change the light received by the detector, thus indicating that the particle Fm is present. Differences between the received light for when the polarizing plate Pf is inserted in the optical path and for when the ND filter is inserted can indicate whether the particle Fm is on the wafer surface or under the surface.

In other words, the polarizing plate Pf can be inserted into the optical path and the semiconductor wafer WF is illuminated, and then the ND filter can be inserted into the optical path and the semiconductor wafer WF can be illuminated with attenuated light from the light source Lm. The optical detector provides separate images for these cases and the brightness of these images is compared. FIG. 10(a) shows a case where the particle Fm is on the wafer surface. In cases like this, the light reflected from the surface of the particle Fm with the polarizing plate Pf inserted and with the ND filter inserted will be roughly identical. Thus, the brightness obtained from the respective images will be similar. This indicates that the particle Fm is present on the wafer surface.

FIG. 10(b) shows a case where the particle Fm is below the surface. In this case, the light passes through the layer Hw2 and is reflected off of the particle Fm. When the polarizing plate Pf is inserted in the optical path and the light is converted to S polarization, this S-polarized light is reflected at the surface of the layer Hw2, i.e., the wafer surface, so that the amount of light reflected off of the particle Fm is low. In contrast, if the ND filter is inserted, the S-polarized light contained in the illuminating light will be reflected off of the wafer surface but a significant amount of light will pass through the layer Hw2 and be reflected off of the particle Fm, thus providing a large amount of reflected light. Thus, compared to the image obtained using the ND filter, the image obtained using the polarizing plate Pf will provide a darker image. This difference in brightness will indicate that the particle Fm is under the surface. The above description can also be applied to defects.

By using the dedicated detecting system shown in FIG. 10 in this manner, the brightness of the obtained images can be compared to determine if a defect is on the wafer surface or under the surface.

FIG. 11 is a drawing showing a dedicated detection system that uses a dark field illumination system. In this detection system, two types of illumination are used: P-polarized light and S-polarized light. Images are obtained for the these two types of illumination.

As shown in FIG. 11(a), if the particle Fm is on the surface, there will be a dark image resulting from P-polarized light illumination, which has a relatively low reflectivity at the surface. A bright image will result from S-polarized light illumination, which has a relatively high reflectivity at the surface. As shown in FIG. 11(b), if the particle Fm is under the surface, there will be a bright image resulting from P-polarized light illumination, which has a relatively low reflectivity at the surface. A dark image will result from S-polarized light illumination, which has a relatively high reflectivity at the surface.

Thus, by comparing the brightness of these two images, the particle Fm can be determined to be on the wafer surface or under the surface. This applies to defects as well.

In the specific examples shown in FIG. 10 and FIG. 11, the illuminated positions on the semiconductor wafer WF are, of course, determined based on the defect position data obtained by the defects inspection device 1 (FIG. 1).

In addition to the methods described above, it would also be possible to determine if a defect is present on the wafer surface or under the surface by carefully measuring the focal point position using a confocal optical system. In addition, inspection data from processes prior to the current inspection process can be used to determine that defects at identical positions are present under the surface.

It would also be possible to use the cause of defects as an attribute. In this case, for defects having identical attributes, images can be acquired for a predetermined number of defects rather than acquiring images for all the defects. Images would not be acquired for the remaining defects. This allows images to be acquired to indicate causes of defects, but detailed inspections for the remaining defects can be omitted, thus further reducing time spent on detailed inspection of defects.

Also, detailed inspections can be performed for a certain number of defects having the same attribute, where this number is based on the number of detected defects having the same attribute. This also reduces the time spent on detailed inspections and also allows the rate at which defects are generated for each attribute to be known.

Also, in the details inspection device 3 and the details inspecting system 27, various conditions can be set up beforehand for each attribute to allow defects to be easily observed with an SEM or to allow image processing to be performed easily. Examples of these conditions include the acceleration voltage and probe current of the SEM, type of detector, work distance, image addition count, and observation angle. This allows images to be acquired under optimal imaging conditions for the particular defect attribute, thus making the acquired image easier to observe. Also using settings suited for image processing will provide stable image processing results.

It would also be possible for defect size to be an attribute so that the SEM imaging magnification can be varied according to size. This allows defect images to be acquired at optimal magnification.

Also, attributes such as defect size can be obtained from pattern inspection devices, and detailed inspections and image acquisition can be performed using the details inspection device 3 or the details inspecting system 27 for defects that are smaller than a particular size. Thus, it is not necessarily required that an extra inspection be performed to add attributes based on output results from an inspection device.

In the embodiments described above, attributes of defects are acquired by the attributes inspection device 2 and the attributes inspecting system 24. However, depending on the attributes to be used, it would be possible to determine attributes with the images used to detect defect positions in the defects inspection device 1 or the defect inspecting system 23. For example, these images can be used to determine defect area (size), perimeter length, color, brightness, texture, relation with background pattern, and the like. By using these singly or in combination as attributes, attributes can be added in parallel with defect inspection.

Also, when determining the attributes used to indicate whether a defect is to be inspected or not in the details inspection device 3 and the details inspecting system 27, a system for setting up evaluation conditions is needed. FIG. 12 shows an example of a detailed inspection performed with an SEM.

In this figure, size, concentration sampling, deletion of defects from previous process, film, circuit, pattern defect, and particle are provided as examples of attributes to be set up.

"Size" is the defect dimension.

"Concentration sampling" indicates the percentage at which to perform random sampling of defects in the detailed inspection when a concentration of defects is detected.

"Delete defects from previous process" indicates that the defect position data from the previous process is to be compared to defect position data from the current process, defect position data overlapping with the data from the previous process is deleted, and new defect data appearing with the current process is to be used.

"Film", "circuit", "pattern defect" and "particle" indicate whether detailed inspections are to be performed for defects having the respective attributes.

The attributes that can be set up are not restricted to the ones above, and any defect characteristic that can be inspected by a details inspection device or a details inspection system can be used.

The method for setting up the evaluation conditions described above can be any system that allows attributes to be associated with "inspect" or "don't inspect". A GUI (Graphics User Interface) is not required, and an editor can be used instead to edit text data or the like. This feature can be provided for each defect inspection device or can be implemented on the data server.

Figure 13:
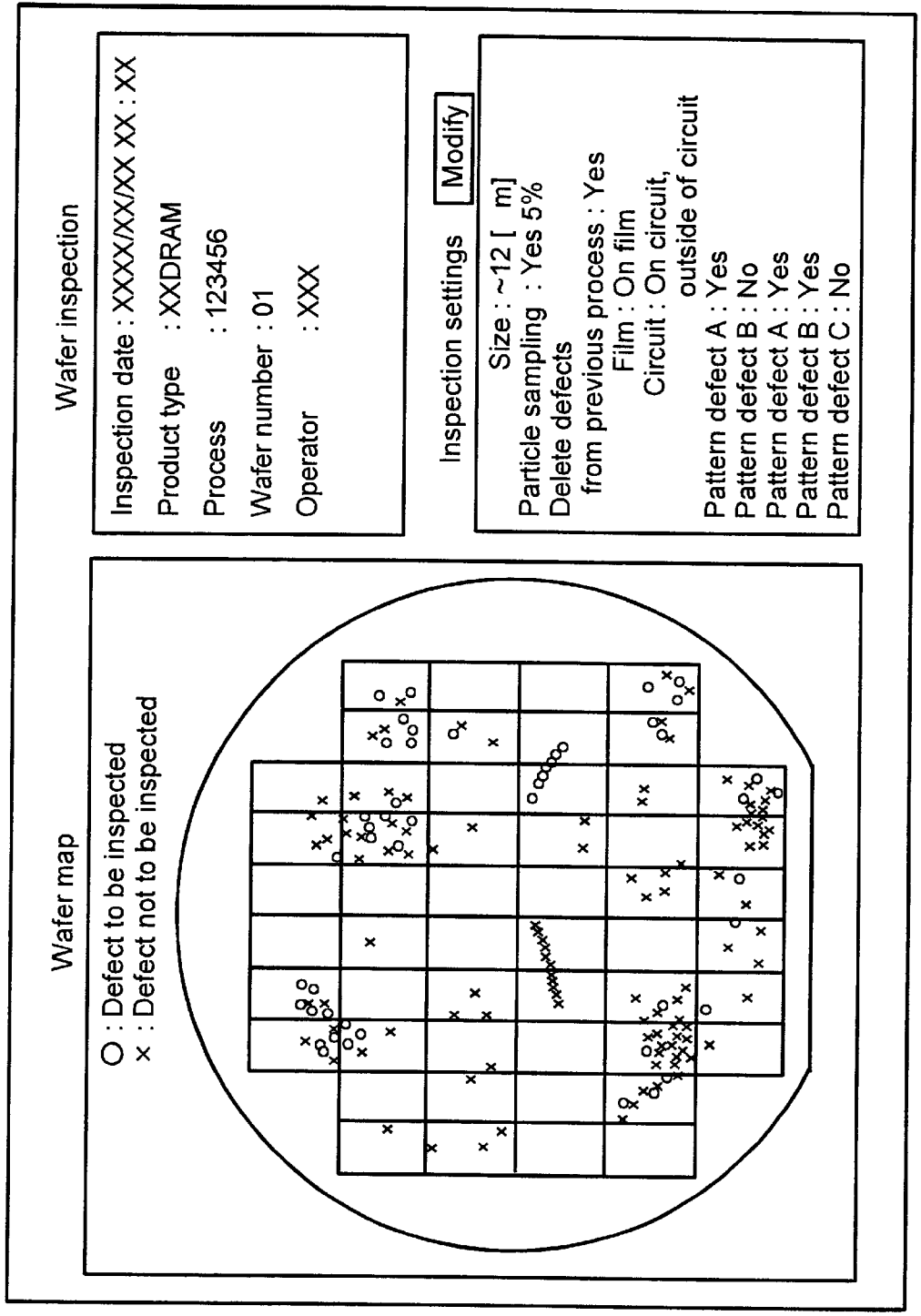
FIG. 13 is a drawing showing a display screen representing the results from the evaluation conditions from FIG. 12.

It would be possible to provide a display on a monitor indicating which defect positions on the semiconductor wafer WF out of the defect position data detected by the defects inspection device 1 from FIG. 1 were selected for inspection based on the conditions set up by the system described above. FIG. 13 shows a specific example of a display screen.

This example shows whether or not detailed inspection is to be performed on a detected defect based on the conditions set up in FIG. 12. A circle indicates a defect to be inspected, and a cross indicates that a defect will not be inspected. The display positions of these defects are based on the defect position data obtained by the defect inspection device.

This display can be provided through the details inspection device 3 or the details inspecting system 27, but it would also be possible to have the data server 7 equipped with a monitor that displays the information. This display can be any type of display that indicates which defects out of the defect position data obtained by the defect inspection will undergo a detailed inspection. Also, attributes to be inspected can be changed after displaying defect positions in this manner.

As described above, the present invention allows whether detailed inspection is to be performed on individual defects detected on a specimen based on attributes added to the defects. This allows detailed inspections to be performed reliably on the defects that require detailed inspections, thus eliminating unnecessary detailed inspections, making the detailed inspections more efficient and reducing the time involved.

Also, the present invention allows the imaging conditions for the detailed inspections to be set up beforehand based on the attributes added to each particle and defect. By changing imaging conditions for detected particles and defects based on their attributes, images can be provided that are easy to observe based on the type of particle or defect. By setting up conditions appropriate for image processing, stable image processing results can be provided.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The preceding has been a description of the preferred embodiment of the invention. It will be appreciated that deviations and modifications can be made without departing from the scope of the invention, which is defined by the appended claims.

What is claimed is:

1. A method for inspecting a specimen comprising:
    detecting defects by inspecting said specimen;
    obtaining attribute information indicating characteristics of said detected defects;
    storing said attribute information in association with position information for said defects;
    determining defects on which to perform detailed inspections out of said defects based on said attribute information;
    determining at least one inspection condition based on said attribute information; and
    performing a detailed inspection of said defects determined for detailed inspection using said at least one inspection condition.

2. A method for inspecting a specimen as described in claim 1 wherein said attribute information is at least one of the following list: area, perimeter length, color, brightness, texture, or relationship with a background pattern of said defect detected by inspecting said specimen.

3. A method for inspecting a specimen as described in claim 1 wherein said attribute information is information relating to an attribute of said defect obtained by means for optical detection.

4. A method for inspecting a specimen as described in claim 1 wherein said attribute information includes information relating to whether or not a defect is present on a surface of said specimen.

5. A method for inspecting a specimen as described in claim 1 wherein selection of whether or not said detailed inspection is to be performed on said defect is based on said attribute information.

6. A method for inspecting a specimen as described in claim 1 wherein said detailed inspection of said defect includes observation of said specimen as described in claim 1 at an angle.

7. A method for inspecting a specimen as described in claim 1 wherein said detailed inspection of said defect is performed using a scanning electron microscope.

8. A method for inspecting a specimen comprising:
inspecting a specimen in a previous inspection process, detecting defects, and storing position information for said detected defects;
inspecting said specimen current inspection process, detecting defects, and storing position information for said detected defects;
acquiring attribute information indicating characteristics of said defects based on said stored position information from said previous inspection process and attribute information indicating characteristics of said defects based on said stored position information from said current inspection process;
associating said position information of said defects with said attribute information;
determining positions of defects on said specimen for which detailed inspection is to be performed, said defects for which detailed inspection is to be performed being determined based on said associated attribute information and said position information; and
performing detailed inspection on defects at said positions determined for detailed inspection, including setting conditions for said detailed inspection based on said attributes.

9. A method for inspecting a specimen as described in claim 8 wherein said attribute information is obtained by comparing said stored position information about defects from said previous inspection process with said stored position information about defects from said current inspection process and deleting information about defects contained in both sets of position information.

10. A device for inspecting defects in a specimen comprising:
means for detecting defects that detects defects on a specimen and obtains position information for said detected defects;
means for extracting attribute information that extracts attribute information for said defects detected by said defect detecting means;
means for storing that stores said defect position information obtained by said defect detecting means in association with said attribute information of said defects extracted by said attribute information extracting means;
means for selecting defects that selects defects for detailed inspection based on said attribute information of said defects stored in said storing means; and
means for performing detailed inspection that performs detailed observation of said defects selected by said defect selecting means, said means for performing detailed inspection including means for setting detailed inspection conditions based on said attribute information.

11. An inspection device as described in claim 10 wherein said defect detecting means optically detects defects on said specimen.

12. An inspection device as described in claim 10 wherein said detailed inspecting means performs detailed inspection on said defects on said specimen by directing an electron beam on said specimen and detecting at least one of a reflected electron and a secondary electron from said specimen generated by said beam.

13. A device for inspecting defects on a specimen comprising:
means for detecting defects that inspects said specimen, detects defects, and outputs position information of said detected defects and information relating to attributes of said defects;
means for storing that stores position information of said defects and information relating to attributes of said defects output from said defect detecting means;
means for selecting that selects defects on which to perform detailed inspection based on said information relating to attributes of said defects stored in said storing means; and
means for performing detailed inspection that performs detailed inspection on said defects selected for detailed inspection by said selecting means, said means for performing detailed inspection including means for setting detailed inspection conditions based on said information relating to attributes.

14. An inspection device as described in claim 13 wherein said defect detecting means includes a defect detector that detects defects on said specimen and an attribute detector that detects attributes of said defects detected by said defect detector.

15. A device for inspecting defects on a specimen comprising:
first means for inspecting including a detector for detecting defect positions on said specimen and an output unit outputting position information of said defects detected by said detector;
second means for inspecting including an information acquiring unit acquiring said position information of said defects output from, said output unit of said first inspecting means, a control unit controlling a position of said specimen based on said defect position information acquired using said information acquiring unit, an inspecting unit inspecting defects of said specimen whose position is controlled by said control unit, an attribute information forming unit forming attribute information based on inspection results from said inspecting unit, an attribute adding unit adding attribute information formed by said attribute information forming unit to said defects inspected by said inspecting unit, and an output unit outputting said defect attribute information added by said attribute adding unit; and
third means for inspecting including an information acquiring unit acquiring said defect attribute information output from said output unit of said second inspecting means, a selecting unit selecting defects on which detailed inspection is to be performed based on said attribute information acquired by said information acquiring unit, and a detailed inspection unit performing detailed inspection of defects selected by said selecting unit and to which said attribute information is attached, said detailed inspection unit configured to set detailed inspection conditions based on said attribute information.

16. An inspection device as described in claim 15 wherein said inspecting unit of said second inspecting means optically inspects said defect attributes.

17. An inspection device as described in claim 15 wherein said detailed inspecting unit of said third inspecting means includes an SEM (scanning electron microscope).

18. An automated inspection apparatus comprising:
at least one of a plurality of inspection stations, comprising:
an adjustable work area that receiving a specimen,
a controller for positioning said adjustable work area,
an inspection apparatus, disposed over said work area to inspect specimens placed on said work area, and a data gathering apparatus that collects information from said inspection apparatus, wherein a first inspection is performed at a first inspection station, resulting in a first set of inspection data comprising information about defects located in said specimen, said first set of inspection data including attributes of said defects, wherein a second inspection is conditionally performed at a second inspection station on selected ones of said defects, said selected ones of said defects being based upon said attributes, wherein one or more inspection conditions for said second inspection are set based on said attributes.

19. The automated inspection apparatus of claim 18, wherein said first set of inspection data further comprises information about a nature of said defects determined as a result of said analyzing said first set of inspection data, and wherein, based upon said nature of said defects, said second inspection is conditionally performed.

20. A method for inspecting a specimen as described in claim 1 wherein said step of determining defects is based on said attribute information of said defects.

21. A method for inspecting a specimen as described in claim 1 wherein said attribute information includes information of a density of the detected defects.

22. A device for inspecting defects in a specimen comprising:

means for detecting defects that detects defects on a specimen and obtains position information for said detected defects;

means for extracting attribute information that extracts attribute information for said defects detected by said defect detecting means;

means for storing that stores said defect position information obtained by said defect detecting means in association with said attribute information of said defects extracted by said attribute information extracting means; and means for selecting defects that selects defects for detailed inspection based on said attribute information of said defects stored in said storing means.

23. A device for inspecting defects on a specimen comprising:

means for detecting defects that inspects said specimen, detects defects, and outputs position information of said detected defects and information relating to attributes of said defects;

means for storing that stores position information of said defects and information relating to attributes of said defects output from said defect detecting means;

means for selecting that selects defects on which to perform detailed inspection based on said information relating to attributes of said defects stored in said storing means.

24. A method for inspecting a specimen comprising:

inspecting said specimen to identify one or more detected defects;

obtaining attribute information indicating characteristics of said one or more detected defects; and identifying candidate defects from among said one or more detected defects for detailed inspection based on said attributes of said one or more detected defects.

* * * * *